United States Patent
DeFranks et al.

(10) Patent No.: US 9,734,815 B2
(45) Date of Patent: Aug. 15, 2017

(54) PILLOW SET WITH SNORING NOISE CANCELLATION

(71) Applicant: DREAMWELL, LTD, Las Vegas, NV (US)

(72) Inventors: Michael S. DeFranks, Atlanta, GA (US); Charles E. Hughes, II, Gastonia, NC (US); Stuart F. Rubin, Orange Village, OH (US)

(73) Assignee: DREAMWELL, LTD, Las Vegas, NV (US)

( * ) Notice: Subject to any disclaimer, the term of this patent is extended or adjusted under 35 U.S.C. 154(b) by 15 days.

(21) Appl. No.: 14/830,765

(22) Filed: Aug. 20, 2015

(65) Prior Publication Data

US 2017/0053637 A1 Feb. 23, 2017

(51) Int. Cl.
*G10K 11/16* (2006.01)
*G10K 11/178* (2006.01)
(Continued)

(52) U.S. Cl.
CPC .............. *G10K 11/178* (2013.01); *A47G 9/10* (2013.01); *A47G 2009/006* (2013.01); *G10K 2210/10* (2013.01)

(58) Field of Classification Search
CPC ................. A47G 9/10; A47G 2009/006; A47G 2009/1018; G10K 2210/505; G10K 2210/116; G10K 11/175; G10K 2210/3027; G10K 2210/3044; G10K 11/1786; G10K 2210/3221; G10K 11/178
See application file for complete search history.

(56) References Cited

U.S. PATENT DOCUMENTS 5,844,996 A * 12/1998 Enzmann ............. A61B 5/7475
381/71.11
8,325,934 B2 12/2012 Kuo
(Continued)

FOREIGN PATENT DOCUMENTS

NO 2011015979 A2 2/2011

OTHER PUBLICATIONS

Notification of Transmittal of the International Search Report and the Written Opinion of the International Searching Authority, or the Declaration, issued in International Application No. PCT/US2016/047515, dated Nov. 25, 2016; 8 pages.
(Continued)

*Primary Examiner* — Muhammad N Edun
(74) *Attorney, Agent, or Firm* — Cantor Colburn LLP

(57) ABSTRACT

Active noise control systems, devices, and methods are disclosed herein. Anti-snoring systems can include a first pillow unit having at least one error microphone and at least one speaker, at least one reference microphone configured to capture sound produced proximate to the at least one reference microphone, and a control unit operatively coupled to the first pillow unit and the at least one reference microphone. In some aspects, the control unit can be configured to produce an anti-noise in the at least one speaker disposed in the first pillow unit by processing signals received from the at least one error microphone and the at least one reference microphone using gated dynamic adjustments such that the anti-noise cancels any sound produced proximate the at least one reference.

20 Claims, 2 Drawing Sheets

(51) Int. Cl.
 *A47G 9/10* (2006.01)
 *A47G 9/00* (2006.01)

(56) References Cited

U.S. PATENT DOCUMENTS

| | | |
|---|---|---|
| 2004/0234080 A1 | 11/2004 | Hernandez et al. |
| 2007/0076896 A1 | 4/2007 | Hosaka et al. |
| 2009/0147965 A1* | 6/2009 | Kuo ............... A47C 21/003 381/71.6 |
| 2010/0302044 A1* | 12/2010 | Chacon ............... A61F 5/56 340/575 |
| 2012/0163626 A1* | 6/2012 | Booij ............... G10K 11/1788 381/92 |
| 2013/0204617 A1 | 8/2013 | Kuo et al. |
| 2014/0169580 A1* | 6/2014 | Levitov ............... G10K 11/178 381/71.6 |

OTHER PUBLICATIONS

Written Opinion of the International Search Authority, issued in International Application No. PCT/US2016/047515, dated Nov. 25, 2016; 8 pages.

* cited by examiner

PILLOW SET WITH SNORING NOISE CANCELLATION

BACKGROUND

The present disclosure generally relates to noise cancelling devices, systems, and methods, specifically to anti-snoring systems and methods producing anti-noise.

Low-frequency noise pollution, such as that caused by snoring, has long been a bane of people sleeping in proximity to one another, such as when sleepers share a bed, room, or are seated in close proximity to one another in transportation settings such as on an airplane. Additionally, other ambient noise such as sirens, traffic, crying babies, and televisions can cause disruptions in sleeping. Snoring, in particular is credited with sleep disruption of a significant portion of sleepers.

Snoring is an acoustic phenomenon generated by vibrating tissue structures due to obstruction in the upper airway during sleep, and is a prominent problem in modern society. Some references, including the U.S. National Commission on Sleep Disorders Research, estimate that about 74 million Americans snore every night, and about 38% of Americans are disturbed by snoring and suffer from daytime fatigue. The intermittent nature of snoring can disrupt the sleep of the snorer's bed partner, causing stress and social nuisance. The sleep disruption has been linked to excessive daytime sleepiness of the snorer and their bed partner. This can result in loss of productivity in the work environment and lead to occupational accidents, or even reduce one's ability to safely operate a car. As mentioned, snore sounds are typically generated by vibrations of the soft palate during sleep and often are nonstationary, intermittent, complex sounds having a transient nature and high short-term sound levels. Additionally, frequency content of snore sounds can change abruptly. As such, actively modeling and canceling snore sounds is difficult.

For low-frequency snoring and other environmental noise, passive methods such as earmuffs or earplugs are either ineffective or uncomfortable to wear during sleep. Several noise cancellation methods have been developed to reduce the noise of snoring utilizing active noise control (referred to herein as "ANC"). These ANC systems are typically based on the principle of super positioning opposing phased sounds to attenuate low-frequency primary (unwanted) noise. That is, ANC systems typically generate a secondary noise of the same magnitude but opposite polarity as the noise sought to be cancelled. As used herein, this secondary noise of the same magnitude but opposite polarity is referred to as "anti-noise." By ANC, the anti-noise and the unwanted noise are both canceled out or their sound pressure level (SPL) is greatly reduced.

For example, ANC systems for abating snoring and other environmental noises have been disclosed. For example, U.S. Pat. No. 8,325,934 to Kuo et al. entitled "Electronic pillow for abating snoring/environmental noises, hands-free communications, and non-invasive monitoring and recording" describes such systems and is incorporated herein by reference in its entirety. Additional systems are described by Sen M. Kuo, et al., in "Active snore noise control systems," which is published in the January-February, 2008 issue of Noise Control Engineering Journal, volume 56(1), which is incorporated herein by reference in its entirety. These systems, however, suffer from several drawbacks, including, among other things, anti-noise speakers that are mounted in less-than-ideal positions as well as the need to have pillows and other bedding units hard-wired to external system components and even other pillows and bedding units. Moreover, ANC systems typically implement dynamic adjustments of anti-noise. These prior art dynamic adjustments cause the systems to converge toward ineffective ANC at least because the dynamic adjustments fail to properly account for periods where no ambient noise is detected, such as in between snores.

Accordingly, there remains a need for improved systems, devices, and methods of abating snoring and other environmental sounds in a sleeping system.

SUMMARY

Active noise control systems, devices, and methods are disclosed herein. In some aspects, an anti-snoring system is disclosed. For example, the anti-snoring system can include a first pillow unit having at least one error microphone and at least one speaker and at least one reference microphone configured to capture sound produced proximate to the at least one reference microphone. The anti-snoring system can also include a control unit operatively coupled to the first pillow unit and the at least one reference microphone such that it receives a signal from the at least one error microphone disposed in the first pillow unit and the at least one reference microphone. Moreover, the control unit can be configured to produce an anti-noise in the at least one speaker disposed in the first pillow unit by processing the signals received from the at least one error microphone and the at least one reference microphone using gated dynamic adjustments such that the anti-noise cancels any sound produced proximate the at least one reference microphone.

In other aspects, anti-snoring systems can include a first pillow unit comprising at least one error microphone and at least one speaker, and a second pillow unit comprising at least one error microphone and at least one speaker. Anti-snoring systems disclosed herein can also include at least one reference microphone configured to capture sound produced proximate to at least one of the first pillow unit and the second pillow unit, and a control unit operatively coupled to the first pillow unit, second pillow unit, and the at least one reference microphone such that it receives a signal from the at least one error microphone in the first pillow, the at least one error microphone in the second pillow, and the at least one reference microphone. In some aspects, the control unit can be configured to produce an anti-noise in the at least one speaker disposed in the first pillow unit by processing the signals received from the at least one error microphone in the first pillow and the at least one reference microphone such that the anti-noise cancels any sound produced proximate the at least one reference microphone.

Also disclosed herein are methods of cancelling sounds. Such methods, for example, include a method of canceling snoring that can include sensing a reference noise with a reference microphone and outputting a reference noise signal to a control unit, sensing an error noise level with an error microphone that is disposed proximate a user's ear and outputting an error noise signal to the control unit, and determining an anti-noise to cancel the reference noise by processing the reference noise signal and the error noise signal using gated dynamic adjustments. The methods can also include producing the anti-noise using at least one speaker that is proximate the user's ear such that the reference noise is cancelled.

The above described and other features are exemplified by the accompanying drawings and detailed description.

BRIEF DESCRIPTION OF THE SEVERAL VIEWS OF THE DRAWINGS

This disclosure will be more fully understood from the following detailed description taken in conjunction with the accompanying drawings, in which.

DETAILED DESCRIPTION

Certain exemplary aspects will now be described to provide an overall understanding of the principles of the structure, function, manufacture, and use of the devices, systems, methods, and/or kits disclosed herein. One or more examples of these aspects are illustrated in the accompanying drawings. Those skilled in the art will understand that the devices, systems, methods, and/or kits disclosed herein and illustrated in the accompanying drawings are non-limiting and exemplary in nature and that the scope of the present invention is defined solely by the claims. The features illustrated or described in connection with any one aspect described can be combined with the features of other aspects. Such modification and variations are intended to be included within the scope of the present disclosure.

Further in the present disclosure, like-numbered components generally have similar features, and thus each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can be determined for any geometric shape. Sizes and shapes of the systems and devices, and the components thereof, can depend at least on the size and shape of the components with which the systems and devices will be used, and the methods and procedures in which the systems and devices will be used.

Noise canceling systems have been developed for use in various applications. For example and without limitation, anti-noise producing systems and devices can be utilized to cancel unwanted ambient noise in a variety of settings. For example, bedding, pillows, headrests, and other devices that are capable of producing anti-noise can be implemented to cancel ambient noise while a user is sleeping. By way of example, pillows may include anti-noise producing components so as to cancel ambient noise such as snoring sounds produced by a bed or roommate. Alternatively, head rests or other seating components, such as those found on airplanes, trains, or buses, can be configured with anti-noise components so as to cancel ambient noise, including talking, snoring, engine noise, announcements, sirens, or any other unwanted ambient noise so as to provide a quiet seating and sleeping environment for passengers.

Figure 1:
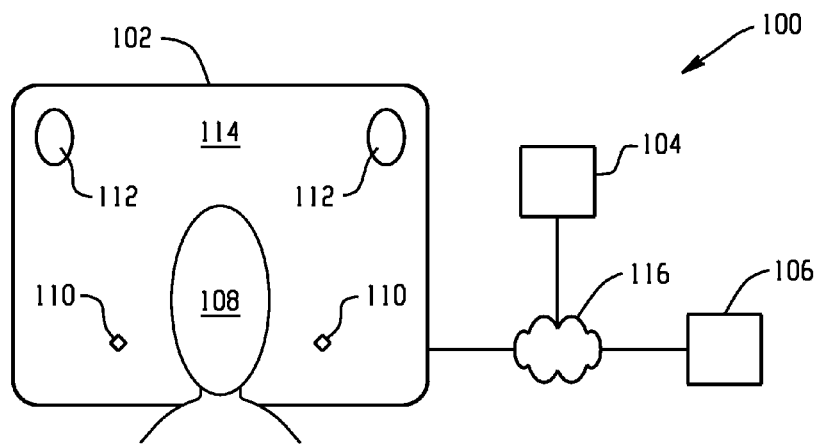
FIG. 1 is a perspective view of an asymmetric anti-snoring device.
Figure 2:
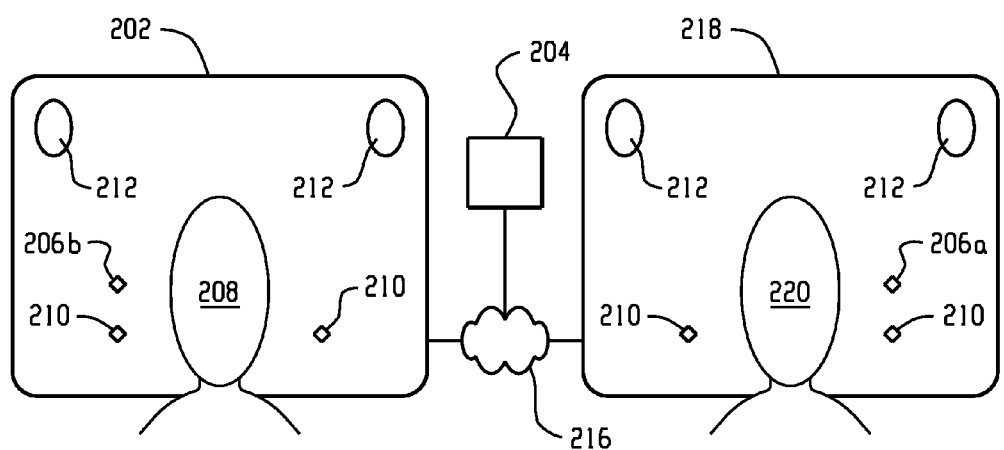
FIG. 2 is a schematic view of a symmetric anti-snoring device.

The systems and methods described herein can be used in asymmetric systems—systems with only one reference microphone unit—or in symmetric systems—systems having more than one reference microphone unit. In at least one aspect, the systems and devices described herein can be employed in a complementary (i.e., symmetric) system such that the system includes a pair of pillow units or other bedding units such that each unit cancels out the sound produced by the user of the other unit. For example, in many applications, a pair of sleepers in a bed will produce noise during the night, i.e., both sleepers snore and not just one. In such scenarios, a complementary system can be employed to cancel out the noise created by each sleeper as opposed to just one. Generally, FIG. 1 illustrates an asymmetric system and FIG. 2 illustrates a complementary system. Such complementary systems, such as that shown in FIG. 2, can include wireless coupling between the complementary pillow units.

FIG. 1 illustrates an asymmetric anti-snoring system 100 having a first pillow unit 102, a control unit 104, and at least one reference microphone 106. In some aspects, the asymmetric anti-snoring system 100 can be configured to produce anti-noise such that user 108 is not disturbed by ambient environmental noise such as snoring.

In some aspects, the first pillow unit 102 is a pillow configured for use by a sleeping user 108 in a bed. In other aspects the pillow unit 102 can be any head-rest unit configured to provide support to the user's head. As such, the first pillow unit 102 can be formed of any known material including a variety of fabrics, leathers, cotton fiber, polyester fiber, rayon fiber, lyocell fiber, polyurethane foam, viscoelastic polyurethane foam, down, goose-down, or any other suitable materials.

The first pillow unit 102, in some aspects, has at least one error microphone 110 and at least one speaker 112. The at least one error microphone can be positioned on or in the pillow unit 102 such that the at least one error microphone is in proximity to the user's 108 ears. Moreover, the at least one speaker can be positioned on or in the pillow unit 102 such that sound emitted from the at least one speaker is easily heard by the user 108. In some aspects, the at least one speaker can also be positioned so that it is not easily heard by persons outside of the area proximal to the sleeping surface 114 of the pillow unit 102, although in some aspects the at least one speaker can be heard by a person outside of the area proximal to the sleeping surface 114 such as the sleeping partner lying in the same bed as the user 108.

The system 100 further includes a control unit 104 operatively coupled to the first pillow unit 102 and the at least one reference microphone 106 such that it receives a signal from the at least one error microphone 110 disposed in the first pillow unit 102 and the at least one reference microphone 106. As shown, the control unit 104 can be connected via an operative coupling 116. As will be discussed in more detail below, the control unit 104 can be configured to produce an anti-noise in the at least one speaker 112 disposed in the first pillow unit 102 by processing the signals received from the at least one error microphone 110 and the at least one reference microphone 106 using gated dynamic adjustments such that the anti-noise cancels any sound produced proximate the at least one reference microphone 106.

The anti-snoring system 100 can also include at least one reference microphone 106 that is configured to capture sound produced proximate to the at least one reference microphone 106. As used herein, "microphone" means any sensor that is capable of detecting a sound. In some aspects, the sound can be a snoring sound made by a snorer within audible proximity to user 108. In other aspects, the sound can be any unwanted environmental sound. In some aspects, more than one pillow unit can be implemented. Such systems are referred to herein as symmetric systems. The at least one reference microphone 106, 206*a*, 206*b* can be positioned in any manner that is suitable to provide causality for the signal processing and operation of the ANC system and generates an audio signal that is sufficiently representative of the acoustical signal to be cancelled by the ANC system. A person of ordinary skill will appreciate, however, that it is not always true that the closer the reference microphone is to the noise source, the better the performance.

As is shown in FIG. 2, for example, an anti-snoring system 200 includes a first pillow unit 202 that is operatively coupled to a control unit 204 and a second pillow unit 218 that includes at least one reference microphone 206*a* disposed on or in the second pillow unit 218. As shown, the at least one reference microphone 206*a* can be disposed on or in the second pillow unit 218 such that the reference microphone 206*a* can detect a snore sound produced by a user 220 of the second pillow unit 218. In some aspects, the first pillow unit 202 can also include at least one reference microphone 206*b*. The at least one reference microphone 206*b* can be disposed on or in the first pillow unit 202 such that the at least one reference microphone 206*b* can detect a snore sound produced by a user 208 of the first pillow unit 202.

An electronic data path between a snorer's pillow and the partner pillow can exist to facilitate ANC processing. As mentioned, in some aspects, the system can use a simple wired path or can include wireless connections. For example, as shown in FIGS. 1-2, the operative coupling 116, 216 can be any coupling that is effective to transmit signals between the inputs and outputs of the control unit, which can include a wired, wireless coupling, or both. In some aspects, as shown in FIG. 2, the operative coupling 216 between the first pillow unit 202, second pillow unit 218, control unit 204, the at least one reference microphone 206*a*, 206*b* can be a wired connection. In other aspects, the system can incorporate a wireless link, such as an RF link, between the system components. For example, the operative coupling 216 between the first pillow unit 202, second pillow unit 218, control unit 204, the at least one reference microphone 206*a*, 206*b*, the at least one error microphones 210, and/or the at least one speakers 212, can be a wireless connection. Any suitable wireless communication hardware and protocol can be employed including radio frequency ("RF"), Bluetooth, wireless personal area networks or wireless local area networks utilizing dedicated microwave, modulated laser light, cellular networks, or any other wireless communication protocol. Moreover, in some aspects, a wireless link can add delay to the system. For example delay can be imposed by the wireless system such as in data packetizing, wireless protocols, and/or encoding/decoding. This delay, however, can be compensated for digitally in the ANC processing algorithm within the control unit, up to a small limiting amount. In some aspects, the delay imposed by the wireless system cannot be in excess of a value that would require the ANC system to operate in a causal manner.

The control unit 104, 204 can include a signal processing unit for sending and receiving signals as well as processing and analyzing signals. The control unit 104, 204 can include various processing components. These components can include, but are not limited to, a power supply, signal amplifiers, at least one computer processor, memory, input and output channels, digital signal processing unit ("DSP"), and/or wireless transmitters and receivers, such as an RF transmitter/receiver. In some aspects, the control unit can be wirelessly coupled to the first bedding unit and the reference unit. As such, the control unit can be any external computing device, including but not limited to bedding control systems such as adjustable and/or hospital bed control systems, smart phones, tablets, and/or personal computers.

As mentioned, the control unit can include a power supply. The power supply can be any suitable power supply including either AC or DC sources. For example, in some embodiments, the power supply can be any of a battery, an AC cord configured to plug in to an AC socket or a DC socket such as a socket that is disposed directly on a bedding unit, inductive coupling sources such as Qi™ produced by Wireless Power Consortium, and/or any other power source.

Figure 3:
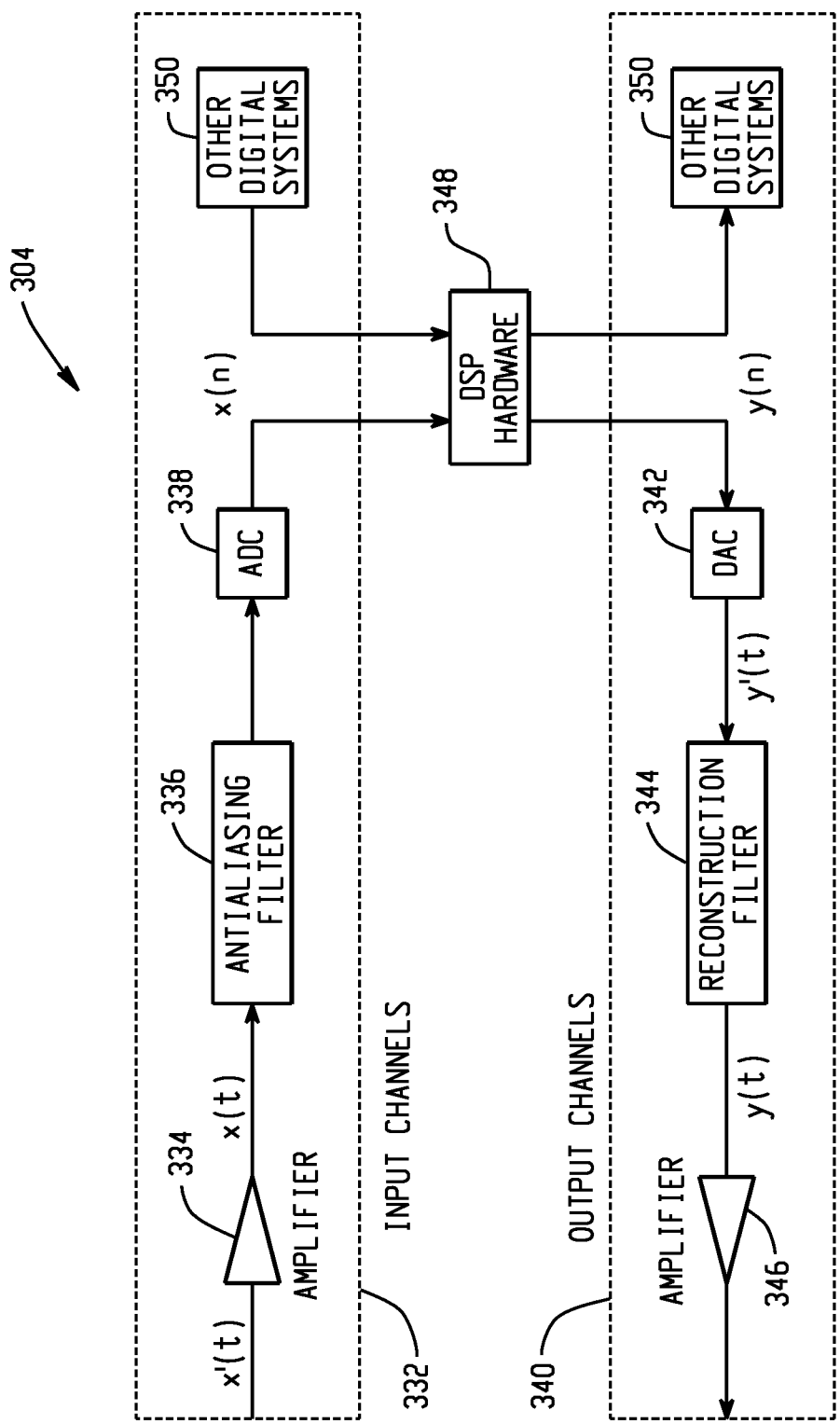
FIG. 3 is a block diagram of a control unit.

As shown in FIG. 3, in some aspects, an example control unit 304 can include at least one input channel 332. In some aspects, the number of input channels 332 can be equal to the total number of error microphones and reference microphones in the anti-snore system. The input channels 332 can be analog, and can include signal conditioning circuitry, a preamplifier 334 with adequate gain, an anti-aliasing low pass filter 336, and an analog-to-digital converter (ADC) 338. The input channels 332 can receive signals (or noise) from the error microphones and the reference microphones.

In some aspects, the control unit 304 can have at least one output channel 340. The number of output channels 340 can be equal to the number of speakers 112, 212 in the anti-snoring system. The output channels 340 can be analog, and can include a digital-to-analog converter (DAC) 342, smoothing (reconstruction) low pass filter 344, and power amplifier 346 to drive the at least one speaker. The output channels 340 can send a signal to the speakers 112, 212 to make sound, such as the desired anti-noise sound.

A digital signal processing unit (DSP) 348 generally includes a processor with memory. The DSP receives signals from the input channels 332 and sends signals to the output channels 340. The DSP can also interface (i.e. input and output) with other digital systems 350, such as, but not limited to, audio players for entertainment, digital storage devices for sound recording and phone interfaces for hands-free communications.

The DSP can also include an algorithm(s) for processing signals for operation of the anti-snoring system. The algorithm(s) can, for example, control interactions between the at least one error microphone 110, 210, the at least one speaker 112, 212, and the at least one reference microphone 1106, 206*a*, 206*b*. In some aspects, the algorithm can be at least one of (a) multiple-channel broadband feedforward active noise control for reducing noise, (b) adaptive acoustic echo cancellation for hands-free communication, (c) signal detection to avoid recording silence periods and sound recognition for non-invasive detection, or (d) integration of active noise control and acoustic echo cancellation. Each of these algorithms are described more fully in U.S. Pat. No. 8,325,934 to Kuo et al. entitled "Electronic pillow for abating snoring/environmental noises, hands-free communications, and non-invasive monitoring and recording," which is incorporated herein by reference in its entirety. The DSP can also include other functions such as non-invasive monitoring using microphone signals and an alarm to wake the user up or call caregivers for emergency situations.

In use, the control unit 304, using the DSP 348, can be configured to further process the input signals using a variety signal processing techniques in order to produce the appropriate anti-noise output signal to be transmitted to the at least one speaker in either the first or second pillow units in such a manner as will avoid improper processing and/or will aid in system functionality. For example, processing methods can be implemented in the DSP 348, as is described below, that limit the improper convergence of the ANC anti-noise signal. By way of example only and without limitation, signal processing methods can include gated dynamic adjustment, primary path training, ultrasonic primary path training, secondary path training, adaptive step size filtering, and automatic gain control. Additionally, auxiliary supplemental audio and sleep analysis functionality can be utilized. Each of these example processing methods and functions is described below.

Gated Dynamic Adjustments

In some aspects, the system can include dynamic adjustment of the adaptive filter. In some prior art applications, the filter is constantly adjusting regardless of whether there is a snore event, silence, or some non-snore sound. This continuous adjustment can lead to a convergence on non-optimal ANC; that is, dynamic adjustments when snores are not occurring can cause the system to improperly adjust, gradually converging toward an ineffective ANC.

In some aspects, a gated dynamic adjustment algorithm or scheme can be used to better adjust during periods of no snoring. "Gated dynamic adjustment" as defined herein means that rather than constantly or continuously adapting a dynamic filter, adjustments to the dynamic filter are dependent on the presence of snoring sounds within certain SPL limits. Using gated dynamic adjustment, a noise gate controlled by the reference microphone can turn the adjustment on when the sound level at the reference microphone exceeds a certain threshold. When the sound is below the threshold, the adjustments are frozen. In this manner, when a new snore event occurs, the adjustments are "ready" and at or near the proper level.

Detection of the snore may be more than simply detecting sound above a threshold. Digital pattern recognition on the reference microphone signal may intelligently determine if the sound is actually a snore or some spurious sound. The adjustments only take place for actual snores or other identifiable, undesirable sounds.

In some aspects, a more complex gate arrangement utilizing "fuzzy logic" controls can be used. Rather than turning the adjustment gate on or off, the fuzzy logic algorithm allows the adjustment control to be partially on following a non-linear function. For example, detecting a quiet snore with low confidence may open the adjustment gate a small amount, but a loud snore may open the gate fully. Multiple inputs other than the simple sound level at the microphone may be inputs to the fuzzy logic system including ambient noise at the reference mic and error mics, confidence in the snore detection, and accelerometers in the snorer's pillow. Fuzzy logic has been shown to be an effective means of controlling non-linear systems which cannot be fully quantified.

Primary Path Training

In a symmetrical system, or in systems employing an additional speaker placed in the snorer's pillow, "primary path training" may be employed. The distance between the at least one reference microphone in the snorer's pillow, and the at least one error microphone in the partner's pillow is defined herein as the "primary path." In some aspects, it can be advantageous to the signal processing to train the system to account for this primary path distance and transmission characteristics, for example to avoid delays associated with the sound traveling the primary path distance. "Primary path training" as used herein is defined as processing a signal received in an error microphone and a reference microphone to account for the distance between the at least one error microphone and the at least one reference microphone. In some aspects, primary path training is accomplished by transmitting a controlled test signal—white or pink noise, for example—from the snorer's speaker and analyzing the received controlled test signal in the error microphones in the partner's pillow and the reference microphone in the snorer's pillow. For example, as shown in FIG. 2, the control unit 204 causes a test signal to play from at least one speaker 212 in the second pillow unit 218. The control unit 204 then analyzes the test signal detected in the at least one error microphone 210 in the first pillow unit 202 and the at least one reference microphone 206a in the second pillow unit 218. In this way, the primary path is quantified and a filter is synthesized. This primary path filter supplements the dynamic filter in the ANC algorithm to achieve closer to ideal cancellation. In some systems, a "secondary path" is trained. That is, a controlled test signal is transmitted from the speakers in a pillow unit to the error microphones within the same a pillow unit. By measuring the response at the error microphones, the acoustic system (speakers, acoustic path, error microphones) is quantified and a filter response is synthesized. This filter response is used to compensate for the non-ideal system response when calculating ANC anti-noise signals.

Ultrasonic Primary Path Training

In some aspects, an inherent constraint to the ANC system is that the primary path distance between the snorer and the at least one error microphone is variable. Primary path training as described above can compensate for this primary path distance but if the primary path changes after training—such as if a sleeping person moves his or her pillow in the night—the primary path training can require adjusting. In some aspects, though, the primary path can be repeatedly trained, for example at least to measure the distance of the primary path, by transmitting an ultrasonic signal between the snorer's pillow and the error microphones. Even as the partners sleep, training can take place as the signal is above the range of human hearing. By transmitting and receiving this ultrasonic signal, the distance of the primary path can constantly or periodically be monitored supplementing the ANC processing computations. In some aspects, ultrasonic primary path training can utilize speakers and microphones having sufficient response capabilities at ultrasonic frequencies and can also include high sampling rate to digitize the ultrasonic signals and present them to a DSP for analysis & processing.

Adaptive Step Size, Mu ($\mu$)

In some aspects, it may be possible to vary the step size, mu ($\mu$), of the adaptive filter (W) to optimize the rate of convergence. Such a process is referred to as "adaptive step size" herein. A relationship between the maximum value of the step size and the length of the adaptive filter may be developed in order to help maintain the stability of the ANC system. In some aspects, the product of the step size and the length of the adaptive filter should be examined and not allowed to exceed a predefined value.

A criterion may be developed to help select the best step size of the adaptive filter to maximize the noise cancellation for a broad range of sound pressure levels (SPL). This criterion would be based on the SPL of the residual noise remaining in the "quiet zone" (around the error microphones & sleep partner's ears) when the ANC is active. This has the benefit of taking the actual SPL of the remaining noise into account for the selection of the step size. This criterion can also be useful for optimizing other parameters of the ANC system.

Automatic Gain Control

In many audio systems there is a large potential dynamic range in the input signals. That is, the difference between the quietest meaningful sound and the loudest can be quite large. This presents a challenge to both the analog electronics (microphones, pre-amplifiers, analog-to-digital-converters, digital-to-analog converters) and digital processing (limited range in fixed-point and to a lesser extent floating-point math). For example, if the input signals are generally quiet, it is natural to have high-gain amplifiers, but if a loud sound suddenly occurs, the systems may "clip," distorting the signal, corrupting or losing information. Conversely, if the gain is set to accommodate the loudest signals, very quiet sounds can be lost in the noise floor of the electronics.

Anti-snore systems can optionally include an automatic gain control (AGC) circuit at one or more points in the audio signal path. As defined herein, "automatic gain control" means a processing algorithm or circuit that provides a controlled signal amplitude at its output, based on the amplitude in the input signal. In this way, the overall dynamic range of the system is increased. In some aspects, during the presence of loud inputs, the gain is lowered. The software is aware of the gain setting and can compensate digitally during processing and the reverse can be true for quiet input signals.

Auxiliary Supplemental Audio

In some aspects, anti-snoring systems can optionally include inputs for auxiliary supplemental audio, i.e., sounds which are intended to be heard, rather than canceled out. For examples, sleep sounds (nature sounds, waves, binaural beats, etc.) can be superimposed with the ANC output on the speaker. Music, television, telephone, or public address audio can also be played by the at least one speaker disposed within either the first or second pillow units or bedding units. In some aspects, the control unit can be operatively coupled to the desired sound producing device, such as a cell phone, television, or public address system such as on an airplane. In some aspects, the control unit can be configured to cease ANC processing during the playback of auxiliary supplemental audio or alternatively can superimpose the auxiliary supplemental audio over the anti-noise produced.

Sleep Analysis

In addition to the error and reference microphones, other sensors can be included in the pillows including accelerometers, thermometers, pressure sensors, heart rate monitors, respiration rate monitors, and any other sensor. These sensors for both the snorer and partner can be used to analyze the sleep state, quality, and quantity of the user's sleep. In some aspects, this data can be transmitted to a computer or smartphone for analysis and snoring may be correlated to the sleep disturbance of the partner. Through analysis of this data, the effectiveness of the snore cancellation and other measures to improve sleep, can be tracked, quantified, and optimized.

In some aspects, a person of ordinary skill will understand that in some ANC systems, the algorithms used to generate anti-noise, such as those described herein, can be sensitive to the input signal's power (or magnitude). If the power of the input signal in certain frequency ranges—for example, less than 100 Hz—has low power either because of the signal itself, the primary path, secondary path, and/or also the frequency response of the microphones or loudspeakers, the convergence of the adaptive filter can be affected and the filter can even diverge in some aspects. As is described below, the primary path and secondary paths of the ANC system, the frequency response of microphones, and the speakers can affect the effectiveness of noise cancellation in certain frequency regions, or maybe the feedback from secondary speaker to the reference sensor. Moreover, as will be appreciated by a person of ordinary skill in the art, the frequency response of system components, such as the at least one error microphone, the at least one response microphone, and the at least one speaker is related to the performance of the ANC system. As such, in some aspects, system components having a desirable response can be included.

Additionally, with respect to sampling frequency and high frequency noises, ANC works well for low frequency noise, for example noise that is generally less than or equal to about 1,000 Hz. In some aspects, ANC can be paired with noise filters configured for high frequency noise, such as noise that is greater than about 1,000 Hz. For example, passive noise controls, including but not limited to noise blocks and noise absorbing foams, can be used. In some aspects, the sampling frequency (or "Fs") can be about 2 kHz and the cut-off frequency of anti-aliasing filters can be approximately 800 Hz, although it will be appreciated that any suitable Fs and cut-off frequencies can be utilized.

Moreover, electronic latency or processing time can be optimized in any given ANC system. Latency can be related to software—for example, processing methods—and the processor's clock speed. In some aspects, sampling frequency and down sampling processing can relate to latency. For example, processes used for buffering samples and down sampling can cause delay. In some aspects, it will be appreciated by a person of ordinary skill in the art that input signals can be processed sample by sample, as opposed to block by block, to limit latency.

With respect to the above description, it is to be realized that the optimum composition is to include variations in components, materials, size, shape, form, function, and manner of operation, assembly and use, are deemed readily apparent to one skilled in the art, and all equivalent relationships to those illustrated in the examples and described in the specification are intended to be encompassed. Therefore, the foregoing is considered as illustrative only. Further, various modifications may be made without departing from the scope thereof, and it is desired, therefore, that only such limitations shall be placed thereon as are set forth in the appended claims.

What is claimed is:

1. An anti-snoring system, comprising:
   a first pillow unit comprising at least one error microphone and at least one speaker;
   a second pillow unit comprising at least one error microphone and at least one speaker;
   at least one reference microphone configured to capture sound produced proximate to at least one of the first pillow unit and the second pillow unit;
   a control unit operatively coupled to the first pillow unit, second pillow unit, and the at least one reference microphone such that it receives signals from the at least one error microphone in the first pillow unit, the at least one error microphone in the second pillow unit, and the at least one reference microphone, and the control unit being configured to produce an anti-noise in the at least one speaker disposed in the first pillow unit by processing the signals received from the at least one error microphone in the first pillow unit and the at least one reference microphone such that the anti-noise cancels any sound produced proximate the at least one reference microphone.

2. The anti-snoring system of claim 1, wherein the control unit is further configured to produce an anti-noise in the at least one speaker disposed in the second pillow unit by processing the signals received from the at least one error microphone in the second pillow unit and the at least one reference microphone using gated dynamic adjustments such that the anti-noise cancels any sound produced proximate the at least one reference microphone.

3. The anti-snoring system of claim 1, wherein the control unit processes the signals using gated dynamic adjustments.

4. The anti-snoring system of claim 1, wherein the control unit further processes the signals using primary path training.

5. The anti-snoring system of claim 1, wherein the control unit further processes the signals using ultrasonic primary path training.

6. The anti-snoring system of claim 1, wherein the control unit further processes the signals using adaptive step size filtering.

7. The anti-snoring system of claim 1, wherein the control unit further processes the signals using automatic gain control.

8. The anti-snoring system of claim 1, wherein the control unit further processes the signals using auxiliary supplemental audio.

9. The anti-snoring system of claim 1, wherein the control unit further processes the signals using sleep analysis.

10. The anti-snoring system of claim 1, wherein processing the signals received from the at least one error microphone in the first pillow unit and the at least one reference microphone further comprises using at least one of primary path training, ultrasonic primary path training, adaptive step size filtering, automatic gain control, auxiliary supplemental audio, and sleep analysis.

11. The anti-snoring system of claim 1, wherein the at least one reference microphone is disposed in at least one of the first pillow unit and the second pillow unit.

12. The anti-snoring system of claim 1, wherein the control unit is disposed within the first pillow unit or second pillow unit.

13. The anti-snoring system of claim 1, wherein the control unit is a smart phone, watch, body-worn computer, pad device, tablet device, or any other self-contained computer processing device on which software can be loaded and executed.

14. The anti-snoring system of claim 1, wherein the at least one error microphone in a first pillow unit can also be used as the at least one reference microphone for generating the anti-noise signal that is produced by the least one speaker in a second pillow unit.

15. The anti-snoring system of claim 14, wherein multiple error microphones are used in a first pillow unit and the signals from each of the multiple error microphones are analyzed to determine which one is best suited to use as the reference signal on which the generated anti-noise that is to be produced by the at least one speaker in the second pillow unit should be based.

16. A method of canceling snoring, comprising:
sensing a reference noise with a reference microphone and outputting a reference noise signal to a control unit;
sensing an error noise level with an error microphone that is disposed proximate a user's ear and outputting an error noise signal to the control unit;
determining an anti-noise to cancel the reference noise by processing the reference noise signal and the error noise signal using gated dynamic adjustments; and
producing the anti-noise using at least one speaker that is proximate the user's ear such that the reference noise is cancelled.

17. The method of claim 16, wherein determining an anti-noise to cancel the reference noise by processing the reference noise signal further comprises utilizing at least one of primary path training, ultrasonic primary path training, adaptive step size filtering, automatic gain control, auxiliary supplemental audio, and sleep analysis.

18. The method of claim 17, wherein the primary path training includes transmitting an ultrasonic signal between a speaker disposed near the reference source and the error microphone that is disposed proximate the user's ear.

19. The method of claim 16, wherein the reference noise is a snoring sound.

20. The method of claim 16, wherein the control unit is wirelessly coupled to at least one of the reference microphone, the error microphone, and the at least one speaker.

* * * * *